(12) United States Patent
Whitfield et al.

(10) Patent No.: US 11,766,255 B2
(45) Date of Patent: *Sep. 26, 2023

(54) SURGICAL INSTRUMENT INCLUDING AN ADAPTER ASSEMBLY AND AN ARTICULATING SURGICAL LOADING UNIT

(71) Applicant: Covidien LP, Mansfield, MA (US)

(72) Inventors: Kenneth Whitfield, North Haven, CT (US); Thomas Casasanta, Southington, CT (US); John W. Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 145 days.

This patent is subject to a terminal disclaimer.

(21) Appl. No.: 17/305,555

(22) Filed: Jul. 9, 2021

(65) Prior Publication Data

US 2021/0361282 A1 Nov. 25, 2021

Related U.S. Application Data

(63) Continuation of application No. 16/695,380, filed on Nov. 26, 2019, now Pat. No. 11,076,850.

(51) Int. Cl.
*A61B 17/072* (2006.01)
*A61B 17/068* (2006.01)
(Continued)

(52) U.S. Cl.
CPC ...... *A61B 17/068* (2013.01); *A61B 17/00234* (2013.01); *A61B 17/072* (2013.01);
(Continued)

(58) Field of Classification Search
CPC ............... A61B 17/068; A61B 17/072; A61B 17/07207; A61B 17/115;
(Continued)

(56) References Cited

U.S. PATENT DOCUMENTS

| 2,777,340 A | 1/1957 | Hettwer et al. |
| 2,957,353 A | 10/1960 | Babacz |

(Continued)

FOREIGN PATENT DOCUMENTS

| CN | 101856251 A | 10/2010 |
| EP | 1759652 A2 | 3/2007 |

(Continued)

OTHER PUBLICATIONS

European Search Report dated Apr. 16, 2021, issued in corresponding EP Appln. No. 20209845, 9 pages.

*Primary Examiner* — Scott A Smith
(74) *Attorney, Agent, or Firm* — Carter, DeLuca & Farrell LLP (57) ABSTRACT

An adapter assembly of a surgical instrument includes a cam member defining a proximal cam slot and a distal cam slot, a first articulation shaft, and a second articulation shaft. The first articulation shaft has a proximal end portion received in the proximal cam slot, and a distal end portion configured to be coupled to a surgical loading unit. The second articulation shaft has a proximal end portion received in the distal cam slot, and a distal end portion configured to be coupled to the surgical loading unit. The first and second articulation shafts are configured to move in opposing longitudinal directions in response to a rotation of the cam member to articulate the surgical loading unit.

20 Claims, 10 Drawing Sheets (51) Int. Cl.
*A61B 17/00* (2006.01)
*A61B 17/29* (2006.01)

(52) U.S. Cl.
CPC ............... *A61B 17/07207* (2013.01); *A61B 2017/00398* (2013.01); *A61B 2017/00477* (2013.01); *A61B 2017/07214* (2013.01); *A61B 2017/07257* (2013.01); *A61B 2017/2913* (2013.01); *A61B 2017/2929* (2013.01)

(58) Field of Classification Search
CPC .......... A61B 2017/00398; A61B 2017/07214; A61B 2017/07257; A61B 2017/07228; A61B 2017/00477; A61B 17/00234; A61B 2017/2929
USPC .............. 227/19, 175.1, 176.1, 175.2, 180.1; 606/1, 139, 219
See application file for complete search history.

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,632,432 A | 5/1997 | Schulze et al. | |
| 5,647,526 A | 7/1997 | Green et al. | |
| 5,653,374 A | 8/1997 | Young et al. | |
| 5,658,300 A | 8/1997 | Bito et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,766,169 A | 6/1998 | Fritzsch et al. | |
| 5,779,130 A | 7/1998 | Alesi et al. | |
| 5,782,396 A | 7/1998 | Mastri et al. | |
| 5,782,397 A | 7/1998 | Koukline | |
| 5,797,536 A | 8/1998 | Smith et al. | |
| 5,820,009 A | 10/1998 | Melling et al. | |
| 5,863,159 A | 1/1999 | Lasko | |
| 5,865,361 A | 2/1999 | Milliman et al. | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,171,316 B1 | 1/2001 | Kovac et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,330,965 B1 | 12/2001 | Milliman et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 6,997,931 B2 | 2/2006 | Sauer et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |
| 7,225,964 B2 | 6/2007 | Mastri et al. | |
| 7,238,021 B1 | 7/2007 | Johnson | |

(56) References Cited

U.S. PATENT DOCUMENTS

| | | |
|---|---|---|
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,245,898 B2 | 8/2012 | Smith et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,351,726 B2 | 5/2016 | Leimbach |
| 9,597,104 B2 | 3/2017 | Nicholas et al. |
| 9,757,126 B2 | 9/2017 | Cappola |
| 9,918,713 B2 | 3/2018 | Zergiebel et al. |
| 11,076,850 B2 | 8/2021 | Whitfield et al. |
| 11,083,458 B2* | 8/2021 | Harris ............... A61B 17/07207 |
| 11,090,075 B2* | 8/2021 | Hunter ................. A61B 17/072 |
| 11,172,929 B2* | 11/2021 | Shelton, IV ............ A61B 34/70 |
| 11,224,428 B2* | 1/2022 | Scott ..................... A61B 90/94 |
| 11,241,230 B2* | 2/2022 | Shelton, IV ....... A61B 17/0682 |
| 11,304,696 B2* | 4/2022 | Shelton, IV ...... A61B 17/07207 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |

(56) References Cited

U.S. PATENT DOCUMENTS

| | | |
|---|---|---|
| 2006/0259073 A1 | 11/2006 | Miyamoto et al. |
| 2006/0273135 A1 | 12/2006 | Beetel |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175956 A1 | 8/2007 | Swayze et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0105750 A1 | 4/2009 | Price et al. |
| 2009/0108048 A1 | 4/2009 | Zemlok et al. |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0206131 A1 | 8/2009 | Weisenburgh, II et al. |
| 2009/0209990 A1 | 8/2009 | Yates et al. |
| 2009/0254094 A1 | 10/2009 | Knapp et al. |
| 2009/0314821 A1 | 12/2009 | Racenet |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0263542 A1 | 9/2014 | Leimbach et al. |
| 2014/0263554 A1 | 9/2014 | Leimbach et al. |
| 2014/0263564 A1 | 9/2014 | Leimbach et al. |
| 2014/0263565 A1 | 9/2014 | Lytle, IV et al. |
| 2014/0276932 A1 | 9/2014 | Williams et al. |
| 2014/0277017 A1 | 9/2014 | Leimbach |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0331375 A1 | 11/2016 | Shelton, IV et al. |
| 2019/0216532 A1 | 7/2019 | Worrell et al. |
| 2021/0153863 A1* | 5/2021 | Whitfield ......... A61B 17/00234 |

FOREIGN PATENT DOCUMENTS

| | | |
|---|---|---|
| EP | 1908412 A2 | 4/2008 |
| EP | 1917929 A1 | 5/2008 |

(56) References Cited

FOREIGN PATENT DOCUMENTS

| | | | |
|---|---|---|---|
| EP | 1952769 | A2 | 8/2008 |
| EP | 2044888 | A2 | 4/2009 |
| EP | 2044890 | A1 | 4/2009 |
| EP | 2090247 | A1 | 8/2009 |
| EP | 2245994 | A1 | 11/2010 |
| EP | 2329773 | A1 | 6/2011 |
| EP | 2377472 | A1 | 10/2011 |
| EP | 2446834 | A1 | 5/2012 |
| EP | 2581055 | A2 | 4/2013 |
| EP | 2612609 | A2 | 7/2013 |
| EP | 2668910 | A2 | 12/2013 |
| EP | 2722011 | A1 | 4/2014 |
| EP | 2815705 | A1 | 12/2014 |
| EP | 2823771 | A1 | 1/2015 |
| EP | 2881046 | A2 | 6/2015 |
| EP | 3725237 | A2 | 10/2020 |
| FR | 2861574 | A1 | 5/2005 |
| KR | 20120022521 | A | 3/2012 |
| WO | 2008121234 | A2 | 10/2008 |
| WO | 2009039506 | A1 | 3/2009 |
| WO | 2009039510 | A1 | 3/2009 |

\* cited by examiner

SURGICAL INSTRUMENT INCLUDING AN ADAPTER ASSEMBLY AND AN ARTICULATING SURGICAL LOADING UNIT

CROSS-REFERENCE TO RELATED APPLICATIONS

This application is a Continuation Application of U.S. patent application Ser. No. 16/695,380, filed on Nov. 26, 2019, now U.S. Pat. No. 11,076,850, the entire contents of which are incorporated by reference herein.

BACKGROUND

Technical Field

The disclosure relates generally to surgical instruments for endoscopic use and, more specifically, to surgical instruments including adapter assemblies that articulate an attached surgical loading unit.

Background of Related Art

Various types of surgical instruments used to endoscopically treat tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument. Typically, surgical stapling instruments include an end effector having an anvil assembly and a cartridge assembly for supporting an array of surgical staples, an approximation mechanism for approximating the cartridge and anvil assemblies, and a firing mechanism for ejecting the surgical staples from the cartridge assembly.

During laparoscopic or endoscopic surgical procedures, access to a surgical site is achieved through a small incision or through a narrow cannula inserted through a small entrance wound in a patient. Because of limited area available to access the surgical site, many endoscopic instruments include mechanisms for articulating the end effector of the instrument in relation to a body portion of the instrument to improve access to tissue to be treated.

SUMMARY

In an aspect of the disclosure, an adapter assembly includes a cam member defining a first cam slot and a second cam slot, an outer tube extending distally from the cam member and having a distal end portion configured to be coupled to a surgical loading unit, and first and second articulation shafts each having a proximal end portion and a distal end portion. The proximal end portion of the first articulation shaft is operably coupled to the proximal cam slot of the cam member and the proximal end portion of the second articulation shaft is operably coupled to the distal cam slot of the cam member. The distal end portion of each of the first and second articulation shafts is configured to be coupled to the surgical loading unit. The first and second articulation shafts are configured to translate in opposite directions in response to a rotation of the cam member to articulate the surgical loading unit relative to the outer tube.

In aspects, the adapter assembly may further include a proximal ring member and a distal ring member each disposed about the cam member. The proximal ring member may have a projection received in the first cam slot, and the distal ring member may have a projection received in the second cam slot. The proximal and distal ring members may be configured to move axially in opposite longitudinal directions in response to the rotation of the cam member.

In aspects, the proximal end portion of the first articulation shaft may be axially restrained to the proximal ring member, and the proximal end portion of the second articulation shaft may be axially restrained to the distal ring member. The first and second articulation shafts may be configured to move axially with the respective proximal and distal ring members.

In aspects, the first and second articulation shafts may be rotatable relative to and about the respective proximal and distal ring members.

In aspects, the proximal ring member may define an outer annular groove therein, and the proximal end portion of the first articulation shaft may have an annular protrusion slidably received in the annular groove. The distal ring member may define an outer annular groove therein, and the proximal end portion of the second articulation shaft may have an annular protrusion slidably received in the annular groove of the distal ring member.

In aspects, the adapter assembly may further include a knob housing disposed about a proximal end portion of the outer tube. The proximal end portion of each of the first and second articulation shafts may be non-rotationally coupled to the knob housing and axially movable relative to the knob housing.

In aspects, the knob housing may include an inner surface defining a pair of longitudinally-extending slots, and the proximal end portion of each of the first and second articulation shafts may have a longitudinally-extending ridge received in the respective pair of longitudinally-extending slots of the knob housing.

In aspects, the proximal end portion of the first articulation shaft may have an inwardly-extending protrusion, and the distal end portion of the outer tube may define a longitudinally-extending slot having received therein the protrusion of the first articulation shaft, such that the distal end portion of the outer tube rotates with the first articulation shaft about the longitudinal axis in response to a rotation of the knob housing.

In aspects, the proximal end portion of each of the first and second articulation shafts may be disposed about the outer tube and the cam member.

In accordance with another aspect of the disclosure, a surgical instrument is provided and includes a surgical loading unit and an adapter assembly. The adapter assembly includes a coupling mechanism having a drive shaft, a cam member operably coupled to the drive shaft and defining a proximal cam slot and a distal cam slot, an outer tube extending distally from the cam member and having a distal end portion configured to be coupled to the surgical loading unit, and first and second articulation shafts each having a proximal end portion and a distal end portion. The proximal end portion of the first articulation shaft is operably coupled to the proximal cam slot of the cam member and the proximal end portion of the second articulation shaft is operably coupled to the distal cam slot of the cam member. The distal end portion of each of the first and second articulation shafts is configured to be coupled to the surgical loading unit. The first and second articulation shafts are configured to translate in opposite directions in response to a rotation of the cam member to articulate the surgical loading unit relative to the outer tube.

In aspects, the adapter assembly may further include a knob housing rotationally coupled to the coupling mechanism and disposed about a proximal end portion of the outer tube. The proximal end portion of each of the first and second articulation shafts may be non-rotationally coupled to the knob housing and axially movable relative to the knob housing.

In aspects, the proximal end portion of each of the first and second articulation shafts may be curved and disposed about the outer tube and the cam member.

BRIEF DESCRIPTION OF THE DRAWINGS

Surgical instruments including exemplary aspects of the the disclosed adapter assemblies are disclosed herein with reference to the drawings, wherein.

DETAILED DESCRIPTION

As used herein, the term "distal" refers to that portion of the surgical instrument which is farthest from a clinician, while the term "proximal" refers to that portion of the surgical instrument which is closest to the clinician. In addition, as used herein, the term clinician refers to medical staff including doctors, nurses and support personnel.

The disclosure is directed to a surgical instrument including an adapter assembly configured to be actuated by a hand-held actuator or a surgical robotic system, and a surgical loading unit coupled to the adapter assembly. The adapter assembly includes an articulation mechanism that drives an articulation of the surgical loading unit relative to the adapter assembly. The articulation mechanism includes a rotatable cam member that defines a pair of cam slots, each of which receiving a corresponding pin of a pair of ring members. As the cam member rotates, the cam slots drive an opposing longitudinal motion of the pair of ring members, which translate first and second articulation shafts in opposing longitudinal directions. Translation of the articulation shafts in opposite longitudinal directions articulates the surgical loading unit relative to an outer tube of the adapter assembly. Additional advantages of the disclosed surgical instruments and components thereof are described below.

Figure 1:
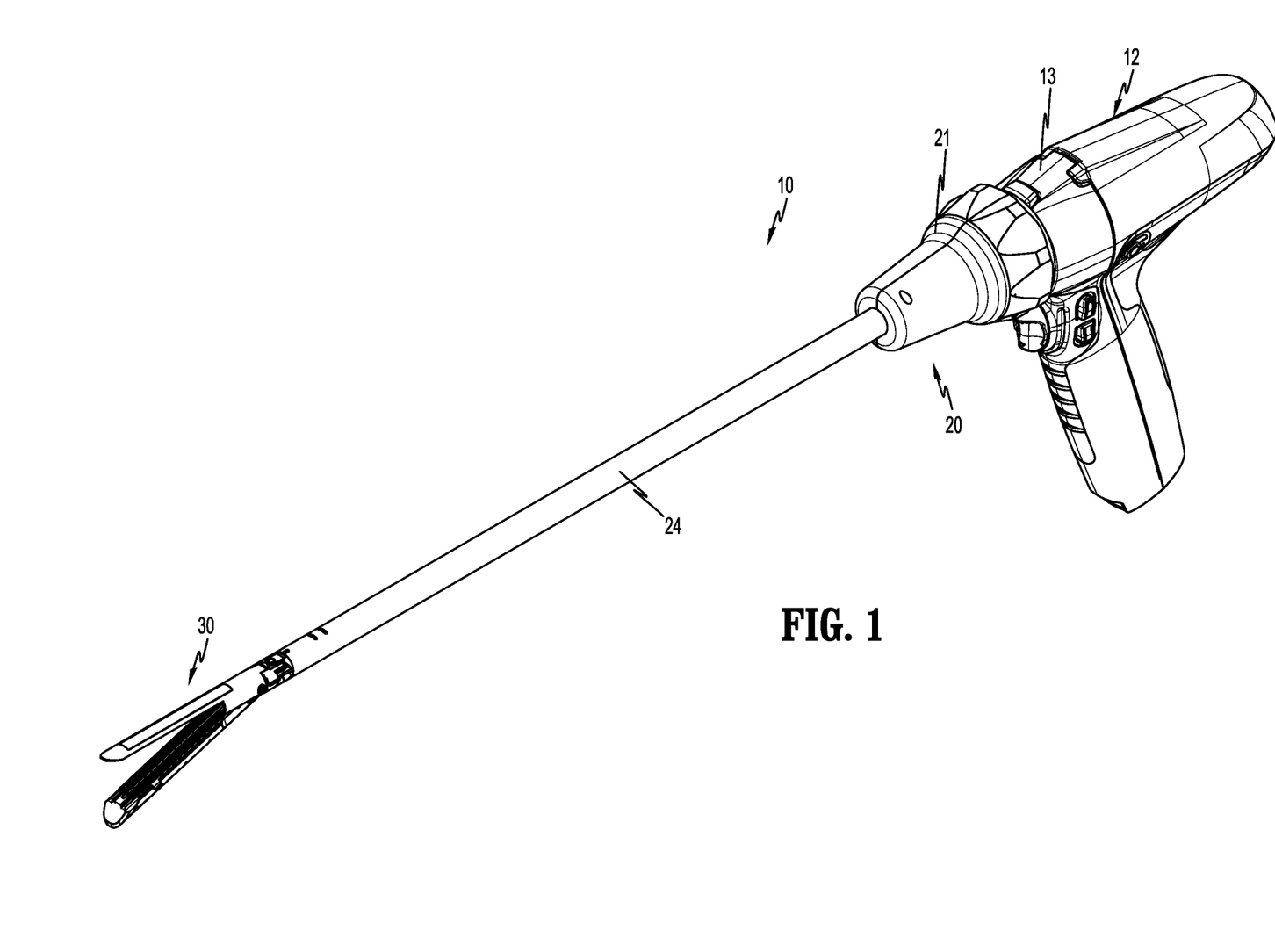
FIG. 1 is a perspective view of a surgical instrument including a handle assembly, an adapter assembly, and a surgical loading unit.
Figure 2:
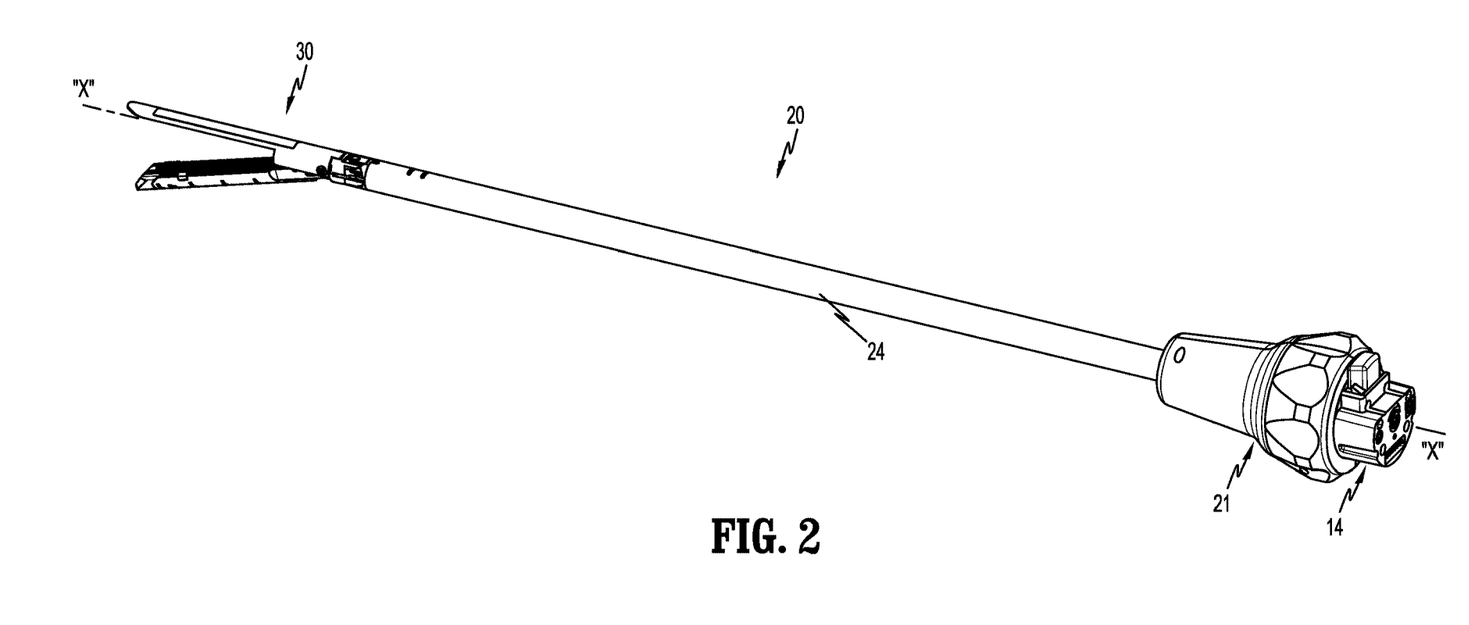
FIG. 2 is a perspective view of the adapter assembly and the surgical loading unit of FIG. 1.

FIGS. 1 and 2 depict a surgical instrument 10 including a handle assembly 12, an adapter assembly 20 configured to be coupled to the handle assembly 12, and a surgical loading unit 30 pivotably coupled to the adapter assembly 20. While the depicted surgical instrument 10 may be configured to fire staples, it is contemplated that the surgical instrument 10 may be adapted to fire any other suitable fastener such as clips and two-part fasteners. Additionally, while the figures depict a linear surgical stapling instrument 10, it is envisioned that certain components described herein may be adapted for use in other types of endoscopic surgical instruments including non-linear surgical stapler loading units, endoscopic forceps, graspers, dissectors, other types of surgical stapling instruments, powered vessel sealing and/or cutting devices, etc.

Figure 3:
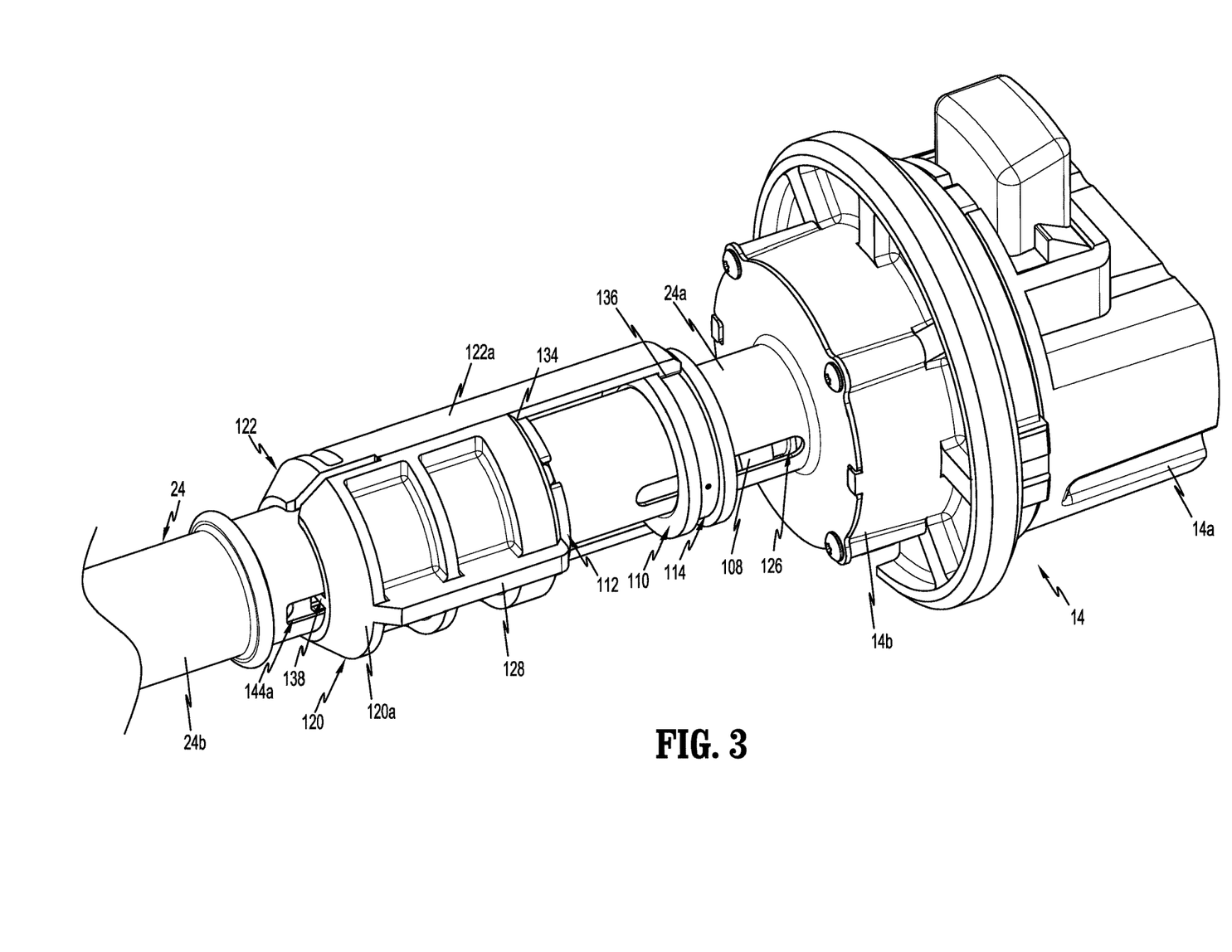
FIG. 3 is a perspective view of internal components of the adapter assembly of FIG. 2 including a coupling mechanism, an outer tube, a pair of ring members, and a pair of articulation shafts.
Figure 4:
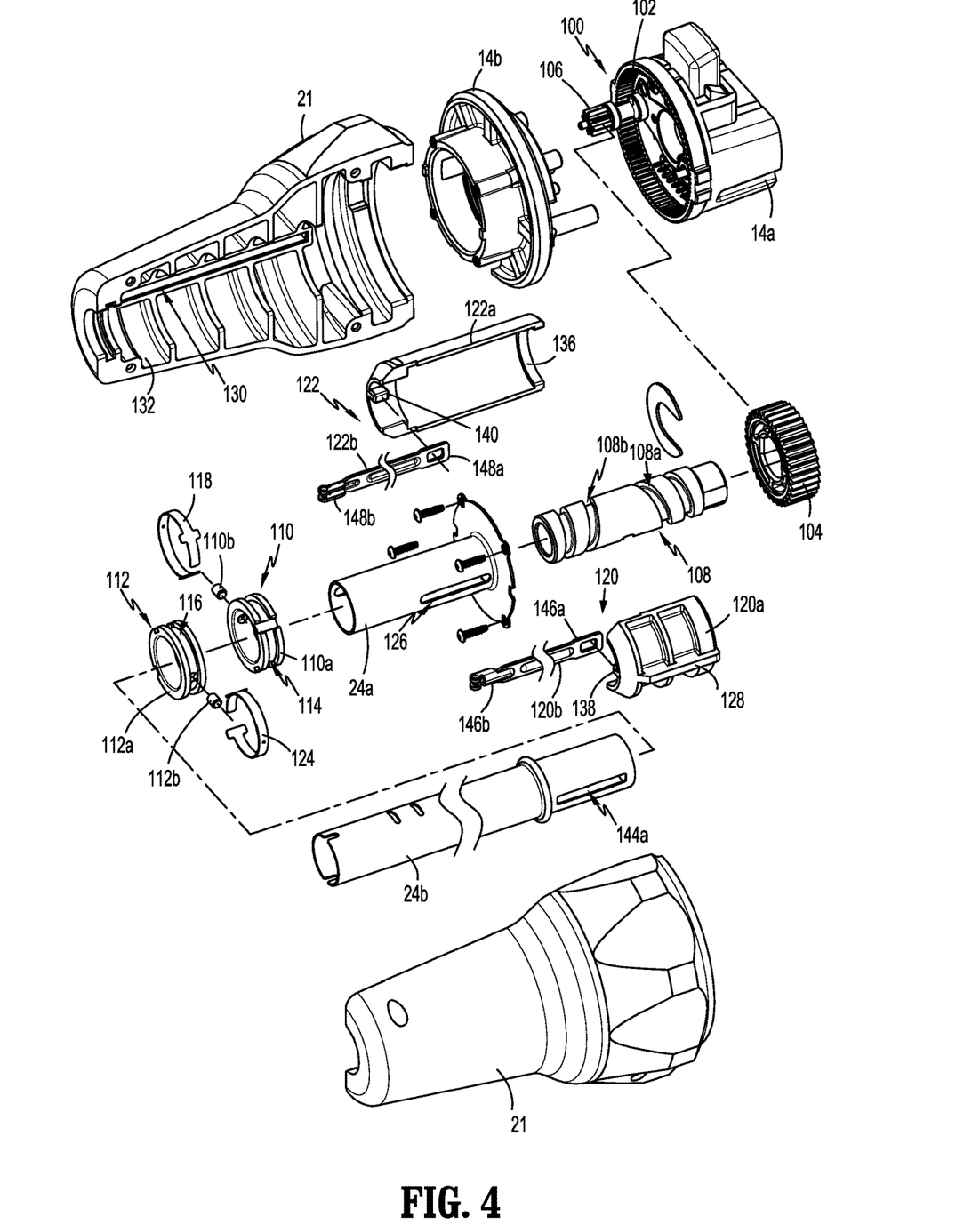
FIG. 4 is a perspective view, with parts separated, of the adapter assembly of FIG. 3.

As shown in FIGS. 2-4, the adapter assembly 20 of the surgical instrument 10 includes a coupling mechanism 14, an outer tube 24 extending distally from the coupling assembly 14, and an outer housing, such as, for example, a rotatable knob housing 21 for manually rotating a distal end portion 24b of the outer tube 24 and the attached surgical loading unit 30. The coupling mechanism 14 is configured to be operably coupled to the handle assembly 12 or a surgical robotic system (not shown) responsible for actuating the surgical instrument 10. The coupling mechanism 14 has a proximal housing 14a (FIG. 3) configured to couple to a distal half-section 13 (FIG. 1) of the handle assembly 12, a distal cap 14b attached to the proximal housing, and a plurality of drive assemblies supported in the proximal housing 14a for transferring actuation forces from motors (not explicitly shown) of the handle assembly 12 to the surgical loading unit 30. For example, one of the drive assemblies is an articulation drive assembly 100 (FIG. 4) including a drive shaft 102 and a rotation gear 104. The drive shaft 102 is rotatably supported by the proximal housing 14a and is configured to receive actuation forces from one of the drive motors of the handle assembly 12. The drive shaft 102 supports a gear 106, such as, for example, a pinion gear that is in meshing engagement with the rotation gear 104 (e.g., a spur gear). The rotation gear 104 is disposed about and fixed to a cam 108 of the adapter assembly 20. In aspects, various alternate types of gears and/or drive transfer mechanisms may be provided, such as, for example, belt drives, miter gears, bevel gears, helical gears, screw gears, or the like.

The outer tube 24 (FIG. 2) of the adapter assembly 20 may be an assembly including a proximal tube 24a (FIG. 3) disposed within the knob housing 21 and a distal tube 24b connected to the proximal tube 24a. The proximal tube 24a is rotationally and axially fixed to the coupling mechanism 14, and the distal tube 24b is configured to rotate with respect to the proximal tube 24a and with the knob housing 21 about a longitudinal axis "X" (FIG. 2) defined by the outer tube 24.

Figure 5:
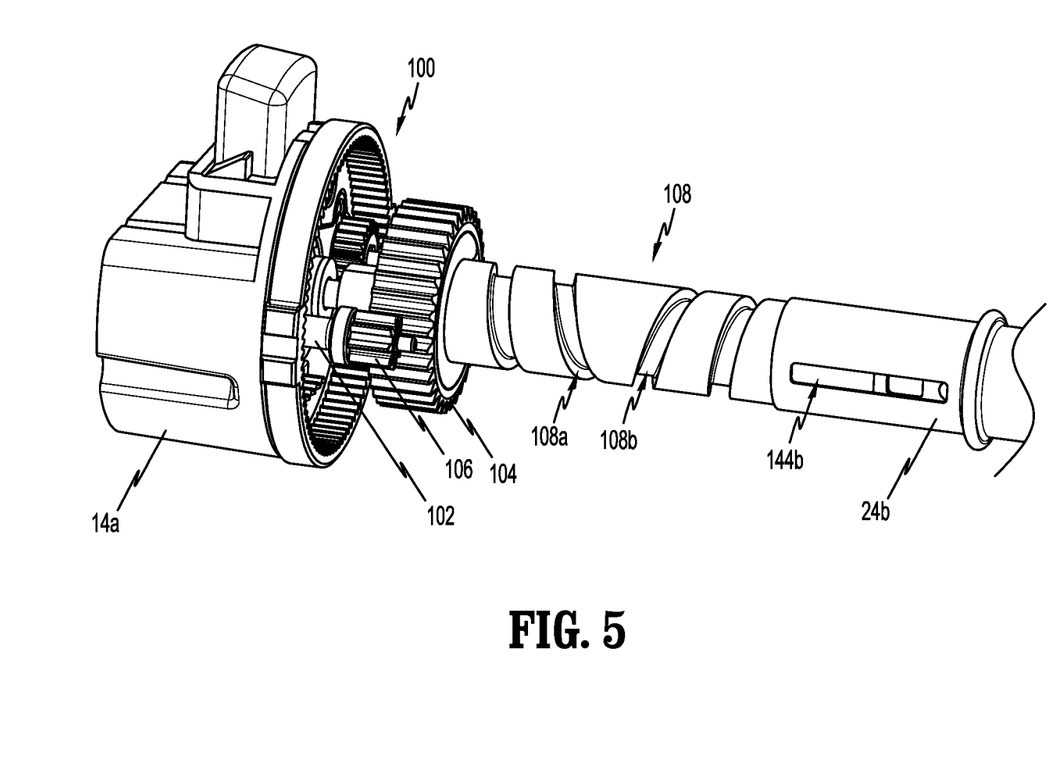
FIG. 5 is a side perspective view illustrating the adapter assembly of FIG. 3, with a portion of the outer tube, the pair of articulation shafts, and the pair of ring members removed to better illustrate a drive assembly and a cam member.
Figures 6, 7:
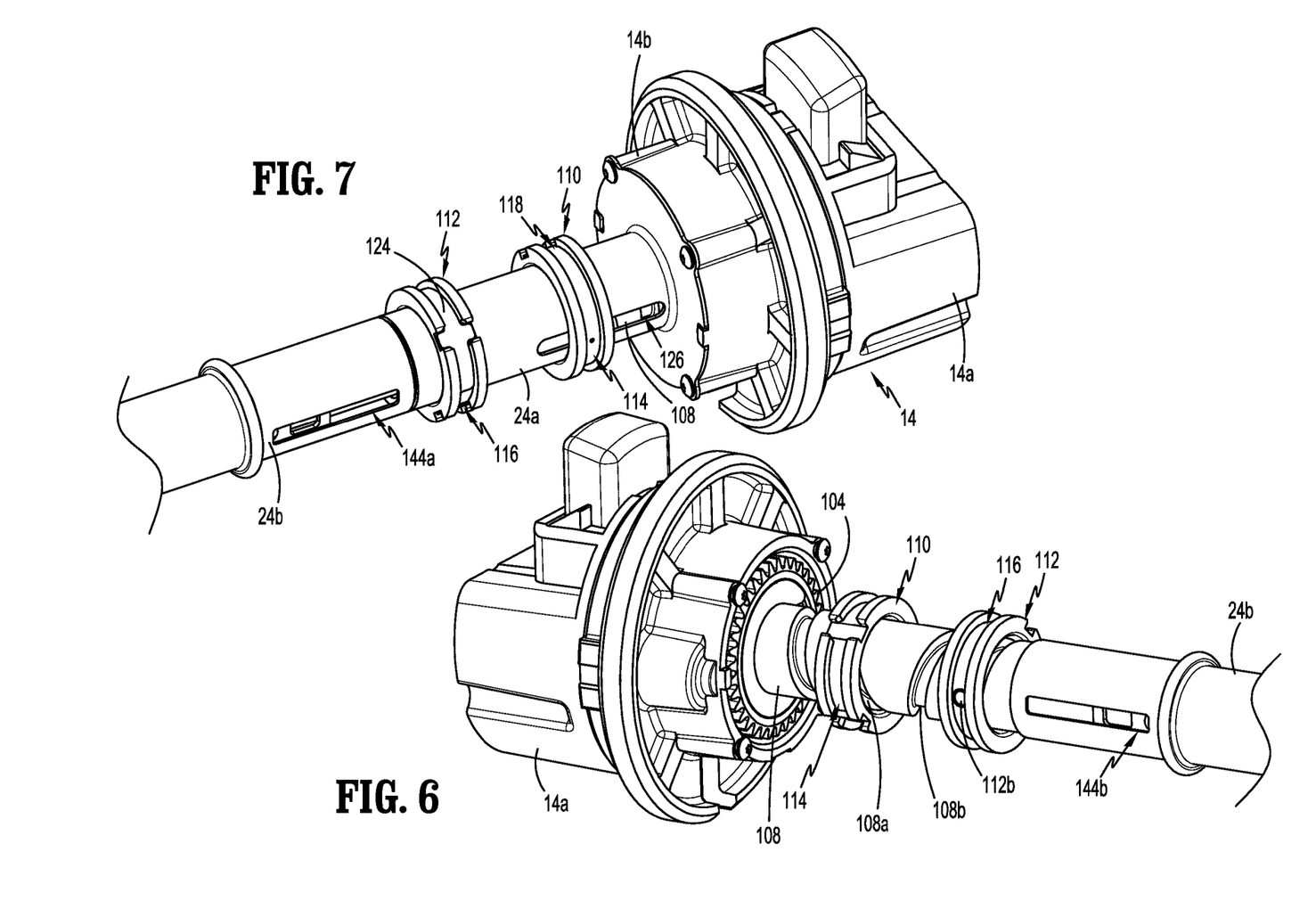
FIG. 6 is a side perspective view illustrating the adapter assembly of FIG. 3, with a portion of the outer tube and the pair of articulation shafts removed.
FIG. 7 is a side perspective view illustrating the adapter assembly of FIG. 3, with the pair of articulation shafts removed.

FIGS. 3-5 illustrate the cam member 108, which may be a tubular shaft or housing that extends through and is rotationally supported in the proximal tube 14a of the outer tube assembly 24. The cam member 108 may be pinned or otherwise non-rotationally coupled to the rotation gear 104 of the coupling mechanism 14, such that the cam member 108 rotates with a rotation of the rotation gear 104. The cam member 108 has a tubular outer surface defining a proximal cam slot 108a and a distal cam slot 108b therein. The proximal and distal cam slots 108a, 108b are longitudinally spaced from one another and wrap around a central longitudinal axis defined by the cam member 108. The proximal and distal cam slots 108a, 108b each have opposite helical configurations. For example, the proximal cam slot 108a may have a left-handed helical configuration, whereas the distal cam slot 108b may have a right-handed helical configuration, or vice versa. In aspects, the proximal and distal cam slots 108a, 108b may each have the same handedness, such as left-handedness or right-handedness.

With reference to FIGS. 3, 4, 6, and 7, the adapter assembly 20 further includes a pair of proximal and distal ring members 110, 112 operably coupled to the cam member 108, a pair of articulation shafts 120, 122 operably coupled to the ring members 110, 112, and a pair of articulation links 150, 152 (FIG. 8) operably coupling the articulation shafts 120, 122 with the surgical loading unit 30. The proximal and distal ring members 110, 112 are each disposed about the proximal tube 24a, with each having a ring body 110a, 112a and a projection 110b, 112b, such as, for example, a pin, extending radially inward from the ring body 110a, 112a. The ring body 110a, 112a of each of the ring members 110, 112 defines an annular groove 114, 116 in an outer surface thereof. A flexible ring-shaped snap retainer 118, 124 may be received in the annular groove 114, 116 to maintain the projections 110b, 112b fixed to the ring bodies 1120a, 112a.

The projection 110b of the proximal ring member 110 extends through a first longitudinally-extending guide slot 126 (FIG. 7) in the proximal tube 24a and is received in the proximal cam slot 108a of the cam member 108. The projection 112b of the distal ring member 112 extends through a second longitudinally-extending guide slot (not explicitly shown) in the proximal tube 24a and is received in the distal cam slot 108b of the cam member 108. The first and second guide slots 126 are disposed on opposite lateral sides of the proximal tube 24a and ensure that the proximal and distal ring members 110, 112 do not rotate during rotation of the cam member 108. Due to the projections 110b, 112b of the proximal and distal ring members 110, 112 being received in the respective proximal and distal cam slots 108a, 108b of the cam member 108, rotation of the cam member 108 translates the proximal and distal ring members 110, 112 in opposite directions along the longitudinal axis "X" of the outer tube 24.

As best shown in FIGS. 3 and 4, the left articulation shaft 120 includes a proximal end portion, such as, for example, a left housing half 120a having a semi-cylindrical configuration, and a distal end portion, such as, for example, an elongate bar 120b extending distally from the left housing half 120a. Similarly, the right articulation shaft 122 includes a proximal end portion, such as, for example, a right housing half 122a having a semi-cylindrical configuration, and a distal end portion, such as, for example, an elongate bar 122b extending distally from the right housing half 122a. The right housing half 122a may be longer than the left housing half 120a, as will be described.

Each of the housing halves 120a, 122a of the left and right articulation shafts 120, 122 has an inwardly-extending, annular protrusion 134, 136 disposed at a proximal end thereof. The annular protrusion 134 of the left housing half 120a is slidably received in the annular groove 114 of the distal ring member 112 due to the left housing half 120a being shorter than the right housing half 122a. The annular protrusion 136 of the right housing half 122a is slidably received in the annular groove 116 of the proximal ring member 110. As such, longitudinal motion of the proximal and distal ring members 110a, 112 is transferred to the respective right and left articulation shafts 122, 120 while allowing for the right and left articulation shafts 122, 120 to rotate about the proximal and distal ring members 110, 112 and with the knob housing 21 (FIG. 4).

An outer surface of each of the housing halves 120a, 122a has a longitudinally-extending ridge 128 (the ridge of the right housing half 122a is not explicitly shown) extending outwardly. Each of the ridges 128 is slidably received in a corresponding longitudinally-extending channel or slot 130 defined in an inner surface 132 of the knob housing 21. The engagement of the ridges 128 of the left and right housing halves 120a, 122a with the channels 130 defined in the opposite sides of the knob housing 21 allows for the left and right articulation shafts 120, 122 to translate relative to and within the knob housing 21 while also forming a non-rotatable engagement with the knob housing 21 such that the articulation shafts 120, 122 are rotatable with the knob housing 21.

The left and right housing halves 120a, 122a of the left and right articulation shafts 120, 122 each further include an inwardly-extending projection or tab 138, 140 (FIG. 3) that extend through respective left and right longitudinally-extending guide slots 144a, 144b defined in the distal tube 24b. The guide slots 144a, 144b in the distal tube 24b allow for the left and right housing halves 120a, 122a to translate relative to the distal tube 24b while non-rotationally coupling the left and right housing halves 120a, 122 to the distal tube 24b.

Figure 8:
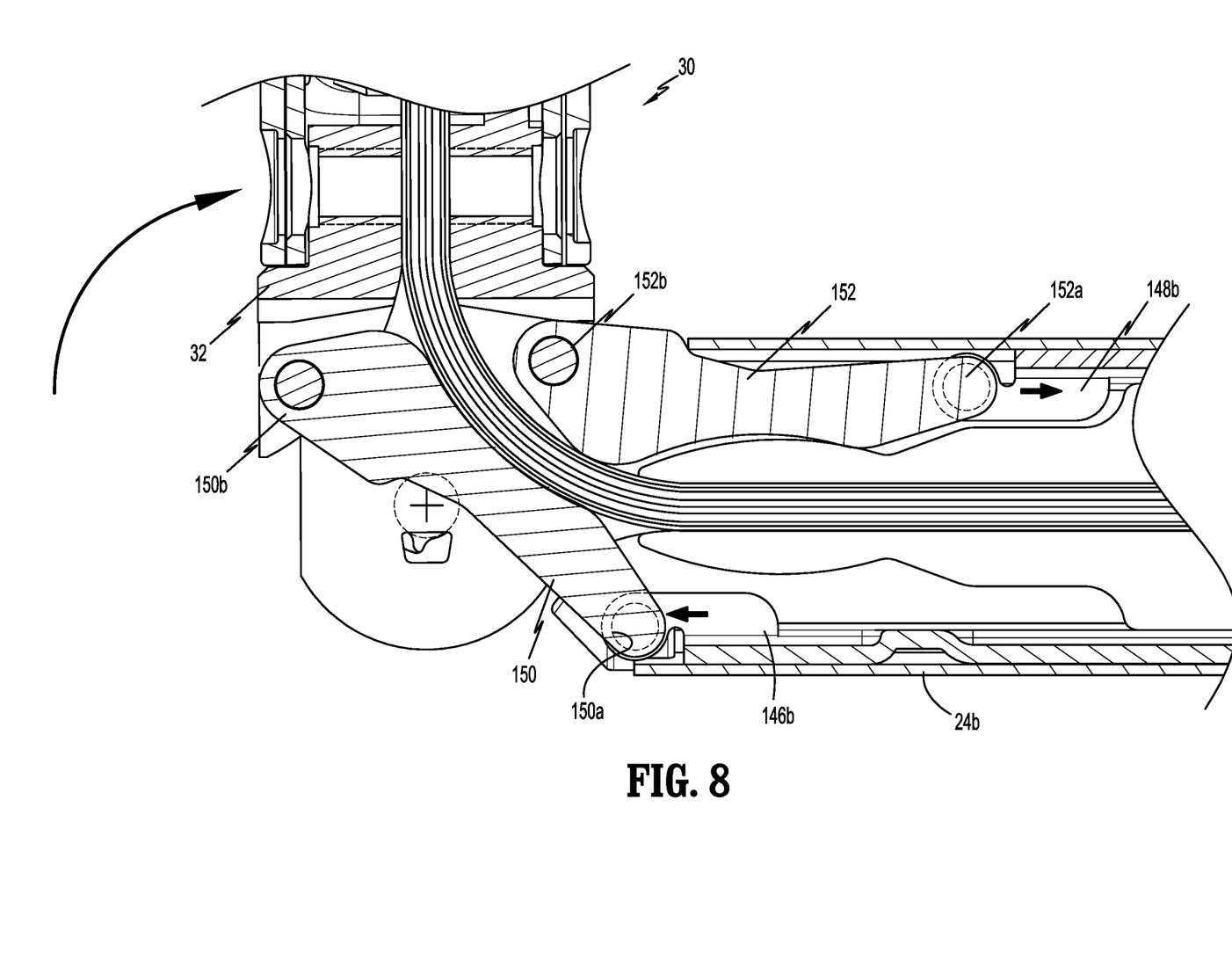
FIG. 8 is a longitudinal cross-sectional view illustrating the surgical loading unit of FIG. 1 in an articulated position.
Figure 9:
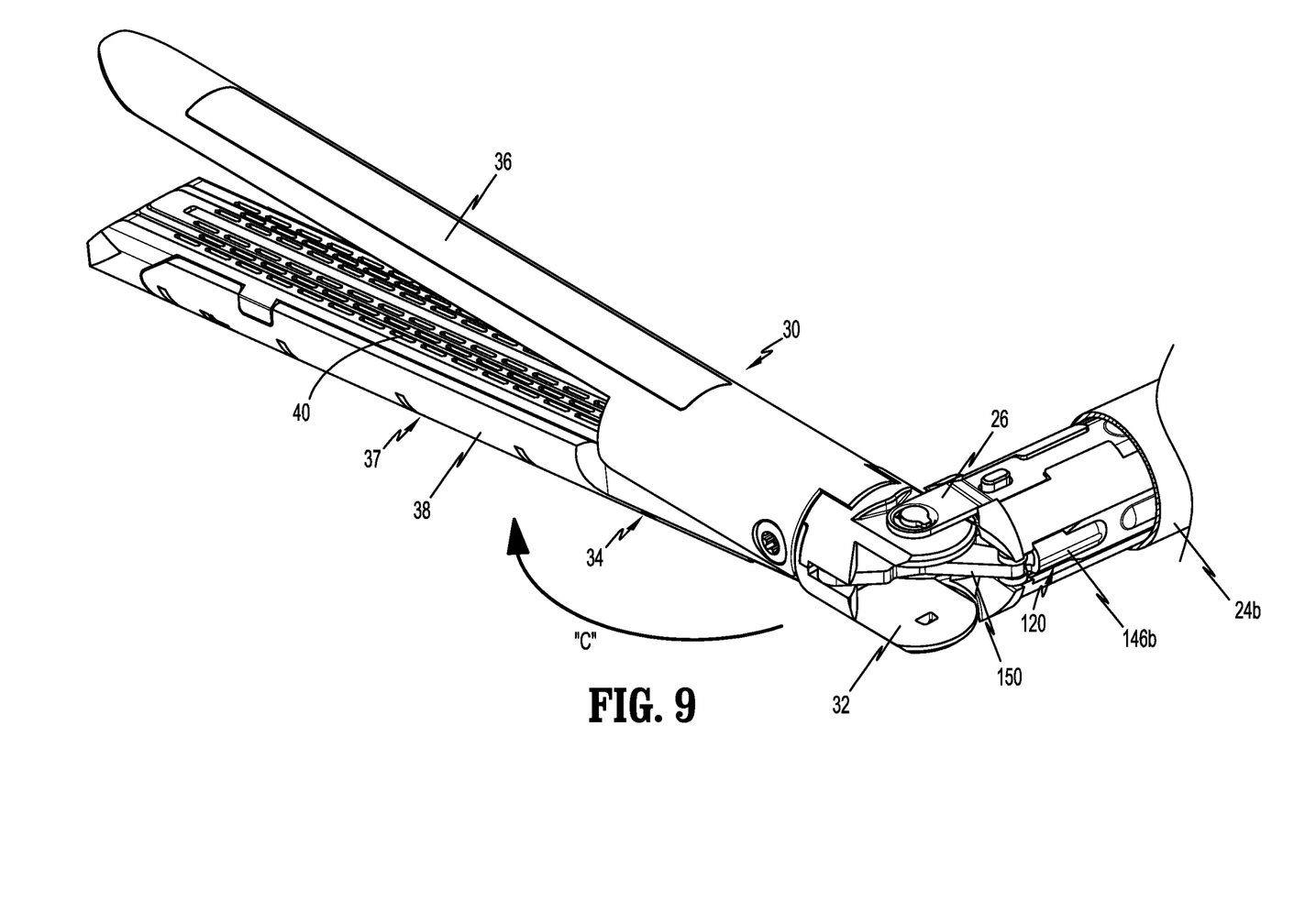
FIG. 9 is a side perspective view illustrating the surgical loading unit of FIG. 1 in the articulated position.

With reference to FIGS. 4, 8, and 9, each of the elongate bars 120b, 122b of the left and right articulation shafts 120, 122 has a proximal end portion 146a, 148a and a distal end portion 146b, 148b. The proximal end portion 146a, 148a of each of the elongate bars 120b, 122b defines an opening having received therein the respective tab 138, 140 of the left and right housing halves 120a, 122a to axially fix the left housing half 120a to the left elongate bar 120b and axially fix the right housing half 122a to the right elongate bar 122b. The left and right elongate bars 120b, 122b of the respective left and right articulation shafts 120, 122 extend distally through the distal tube 24b and terminate distally at a distal end of the distal tube 24b.

The first articulation link 150 (FIG. 8) has a proximal end portion 150a pivotably coupled to the distal end portion 146b of the left elongate bar 120b, and the second articulation link 152 has a proximal end portion 152a pivotably coupled to the distal end portion 148b of the right elongate bar 122b. In aspects, the first and second articulation links 150, 152 may be coupled to the first and second elongate bars 120b, 122b via intermediary shafts (not explicitly shown). The first and second links 150, 152 each have a distal end portion 150b, 152b pivotably coupled to opposite sides of a collar 32 of the surgical loading unit 30. As such, the opposing longitudinal motion of the first and second articulation shafts 120, 122, induced by a rotation of the cam member 108, pushes and pulls the corresponding first and second links 150, 152 to articulate the surgical loading unit 30 relative to the adapter assembly 20.

The surgical loading unit 30 is adapted to be attached to the distal tube 24b of the adapter assembly 20 and may be configured for a single use, or may be configured to be used more than once. A pivot joint 26 (FIG. 9) is pivotably coupled to the distal tube 24b and axially restrained thereto. The pivot joint 26 is configured to pivotably support the collar 32 of the surgical loading unit 30 thereto. The surgical loading unit 30 includes an end effector 34 supported on the collar 32. The end effector 34 includes an anvil plate 36 non-rotationally coupled to the collar 32, and a staple cartridge assembly 37 disposed in opposed relation with the anvil plate 36. The staple cartridge assembly 37 has a chassis 38 pivotably coupled to the collar 32 and a staple cartridge body 40 configured for removable receipt in a channel of the chassis 38. A knife rod (not explicitly shown) is translatable through the end effector 34 to cut tissue disposed therebetween. The knife rod is further configured to selectively open and close the end effector 34 and fire staples therefrom as it translates through the end effector 34.

Figure 10:
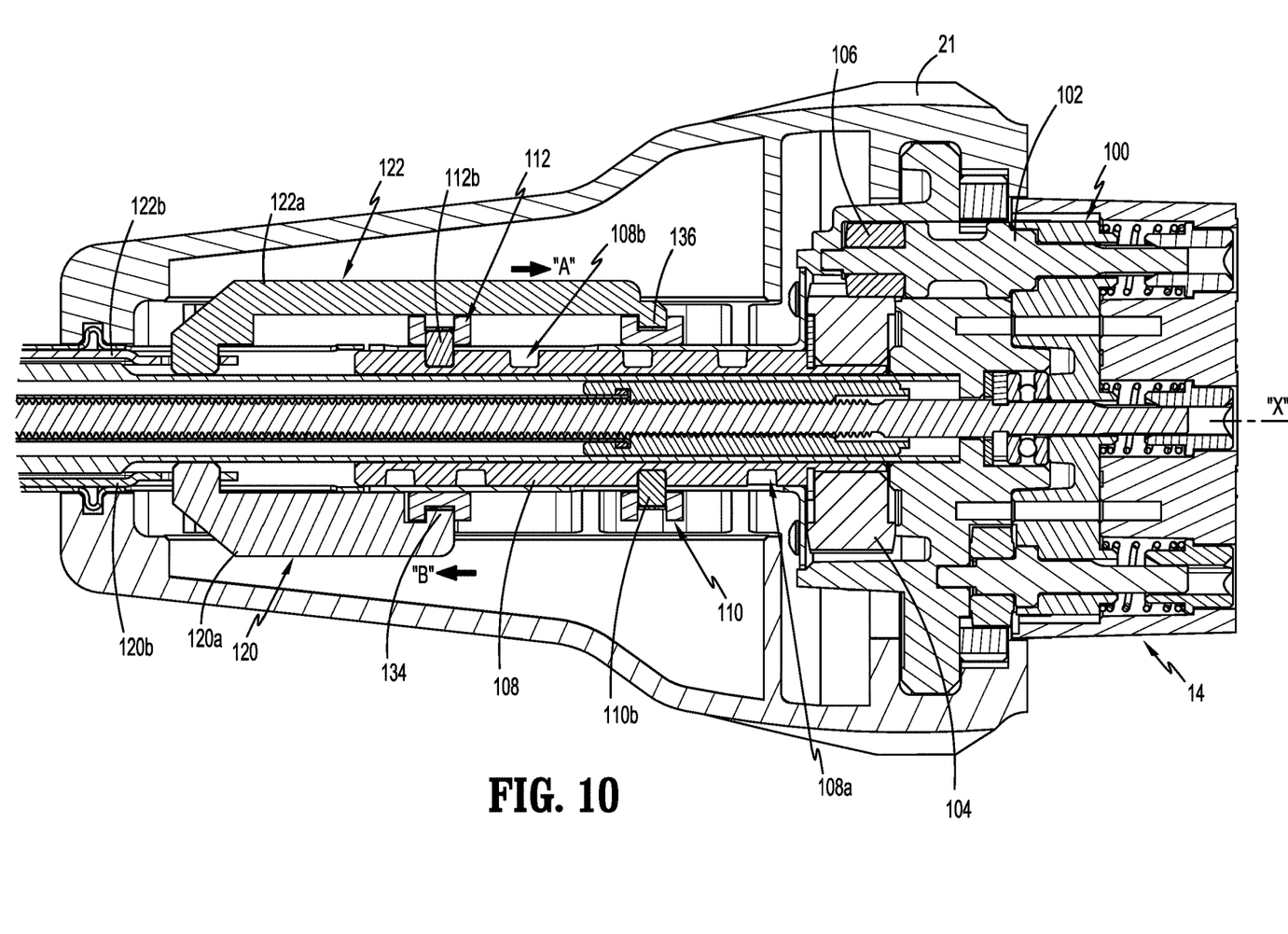
FIG. 10 is a longitudinal cross sectional view of the adapter assembly of FIG. 3 illustrating the pair of articulation shafts in a non-articulated position.
Figure 11:
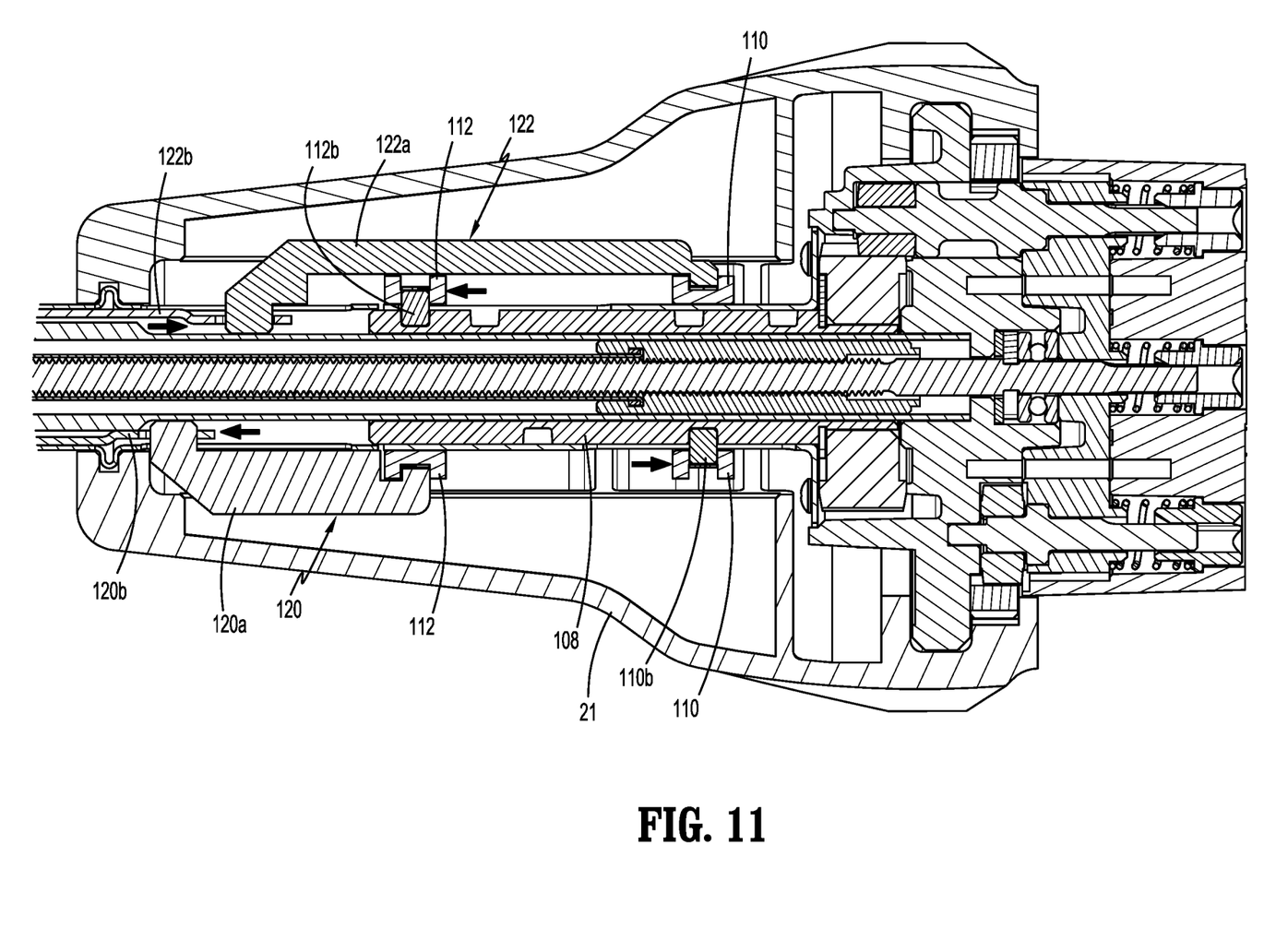
FIG. 11 is a longitudinal cross sectional view of the adapter assembly of FIG. 3 illustrating the pair of articulation shafts in an articulated position.

In operation, with reference to FIGS. 10 and 11, to articulate the surgical loading unit 30, the drive shaft 102 of the articulation drive assembly 100 is rotated via an actuation of the handle assembly 12 (FIG. 1). The drive shaft 102 transfers rotational motion from the gear 106 fixed thereabout to the rotation gear 104. Since the cam member 108 is fixed to the rotation gear 104 (FIG. 5), the cam member 108 rotates with the rotation gear 104 about the central longitudinal axis "X" of the outer tube 24. As the cam member 108 rotates, the proximal cam slot 108a of the cam member 108 drives the pin 110a of the proximal ring member 110 through the proximal cam slot 108a in a proximal direction and the distal cam slot 108b of the cam member 108 drives the pin 112b of the distal ring member 112 through the distal cam slot 108b in a distal direction.

The proximal movement of the proximal ring member 110 drives a proximal movement of the right articulation shaft 122, in the direction indicated by arrow "A" in FIG. 10, due to the engagement of the right housing half 122a of the right articulation shaft 122 with the proximal ring member 110. Similarly, the distal movement of the distal ring member 112 drives a distal movement of the left articulation shaft 120, in the direction indicated by arrow "B" in FIG. 10, due to the engagement of the left housing half 120a of the left articulation shaft 120 with the distal ring member 112. As such, the right and left articulation shafts 122, 120 are moved from a first position (FIG. 10) corresponding to a non-articulated orientation of the surgical loading unit 30 (i.e., the surgical loading unit 30 is coaxial with the outer tube 24) to a second position (FIG. 11) corresponding to an articulated orientation of the surgical loading unit 30 (i.e., the surgical loading unit 30 is pivoted to a non-parallel angle relative to the outer tube 24, FIG. 9).

In particular, due to the first articulation link 150 acting as a pivotable coupling between the left articulation shaft 120 of the adapter assembly 20 and the left side of the surgical loading unit 30, and the second articulation link 152 acting as a pivotable coupling between the right articulation shaft 122 of the adapter assembly 20 and the right side of the surgical loading unit 30, proximal movement of the right articulation shaft 122 and distal movement of the left articulation shaft 120 drives an articulation of the surgical loading unit 30 in the right direction indicated by arrow "C" in FIG. 9. It is contemplated that a rotation of the cam member 108 in the opposite direction results in an articulation of the surgical loading unit 30 in the left direction.

To rotate the surgical loading unit 30 about the longitudinal axis "X" of the outer tube 24, the knob housing 21 may be manually rotated about the longitudinal axis "X." Since the ridge 128 (FIG. 3) of the left housing half 120a is captured in the left channel (not shown) in the knob housing 21, and the ridge (not shown) of the right housing half 122a is captured in the right channel 130 (FIG. 4) in the knob housing 21, the left and right articulation shafts 120, 122 rotate with the rotation of the knob housing 21. The arcuate grooves 114, 116 in the proximal and distal ring members 110, 112 allow for the left and right articulation shafts 120, 122 to rotate relative to and around the proximal and distal ring gears 110, 112 during the rotation of the knob housing 21. Further, since the projection 138 of the left housing half 120a is received in the left slot 144a in the distal tube 24b, and the projection 140 of the right housing half 122a is received in the right slot 144b in the distal tube 24b, rotation of the left and right articulation shafts 120, 122 induces a corresponding rotation of the distal tube 24b relative to the proximal tube 24a, whereby the attached surgical loading unit 30 is also caused to rotate about the longitudinal axis "X."

Persons skilled in the art will understand that the adapter assemblies and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. An adapter assembly, comprising:
   a cam member defining a first cam slot and a second cam slot;
   a first articulation shaft having a proximal end portion operably coupled to the first cam slot of the cam member, and a distal end portion configured to be coupled to a surgical loading unit; and
   a second articulation shaft having a proximal end portion operably coupled to the second cam slot of the cam member, and a distal end portion configured to be coupled to the surgical loading unit, wherein the first and second articulation shafts are configured to translate in opposite directions in response to a rotation of the cam member to articulate the surgical loading unit.

2. The adapter assembly according to claim 1, wherein the first and second articulation shafts are movable relative to the cam member along an annular path.

3. The adapter assembly according to claim 1, further comprising:
   a proximal ring member disposed about the cam member and having a projection received in the first cam slot; and
   a distal ring member disposed about the cam member and having a projection received in the second cam slot, wherein the proximal and distal ring members are configured to move axially in opposite longitudinal directions in response to the rotation of the cam member.

4. The adapter assembly according to claim 3, wherein the proximal end portion of the first articulation shaft is axially restrained to the proximal ring member, and the proximal end portion of the second articulation shaft is axially restrained to the distal ring member, such that the first and second articulation shafts are configured to move axially with the respective proximal and distal ring members.

5. The adapter assembly according to claim 4, wherein the first and second articulation shafts are rotatable relative to and about the respective proximal and distal ring members.

6. The adapter assembly according to claim 5, wherein the proximal ring member defines an outer annular groove therein, and the proximal end portion of the first articulation shaft has a protrusion slidably received in the annular groove.

7. The adapter assembly according to claim 6, wherein the distal ring member defines an outer annular groove therein, and the proximal end portion of the second articulation shaft has a protrusion slidably received in the annular groove of the distal ring member.

8. The adapter assembly according to claim 5, further comprising a knob housing, wherein the proximal end portion of each of the first and second articulation shafts is non-rotationally coupled to the knob housing and axially movable relative to the knob housing.

9. The adapter assembly according to claim 8, wherein the knob housing includes an inner surface defining a pair of slots, and the proximal end portion of each of the first and second articulation shafts has a ridge received in the respective pair of slots of the knob housing.

10. The adapter assembly according to claim 1, wherein the proximal end portion of each of the first and second articulation shafts is disposed about the cam member.

11. A surgical instrument, comprising:
   a drive shaft;
   a cam member operably coupled to the drive shaft and defining a proximal cam slot and a distal cam slot;
   a first articulation shaft having a proximal end portion operably coupled to the proximal cam slot of the cam member, and a distal end portion configured to be coupled to a surgical loading unit; and
   a second articulation shaft having a proximal end portion operably coupled to the distal cam slot of the cam member, and a distal end portion configured to be coupled to the surgical loading unit, wherein the first and second articulation shafts are configured to translate in opposite directions in response to a rotation of the cam member to articulate the surgical loading unit.

12. The surgical instrument according to claim 11, further comprising an outer shaft extending distally from the cam member and having a distal end portion configured to be coupled to the surgical loading unit.

13. The surgical instrument according to claim 12, further comprising a knob housing disposed about a proximal end portion of the outer shaft, wherein the proximal end portion of each of the first and second articulation shafts is non-rotationally coupled to the knob housing and axially movable relative to the knob housing.

14. The surgical instrument according to claim 13, wherein the knob housing includes an inner surface defining a pair of slots, and the proximal end portion of each of the first and second articulation shafts has a ridge received in the respective pair of slots of the knob housing.

15. The surgical instrument according to claim 13, wherein the proximal end portion of the first articulation shaft has an inwardly-extending protrusion, and the distal end portion of the outer shaft defines a longitudinally-extending slot having received therein the protrusion of the first articulation shaft, such that the distal end portion of the outer shaft rotates with the first articulation shaft about the longitudinal axis in response to a rotation of the knob housing.

16. The surgical instrument according to claim 11, further comprising:
   a proximal ring member disposed about the cam member and having a projection received in the proximal cam slot; and
   a distal ring member disposed about the cam member and having a projection received in the distal cam slot, wherein the proximal and distal ring members are configured to move axially in opposite longitudinal directions in response to the rotation of the cam member.

17. The surgical instrument according to claim 16, wherein the proximal end portion of the first articulation shaft is axially restrained to the proximal ring member, and the proximal end portion of the second articulation shaft is axially restrained to the distal ring member, such that the first and second articulation shafts are configured to move axially with the respective proximal and distal ring members.

18. The surgical instrument according to claim 17, wherein the first and second articulation shafts are rotatable relative to and about the respective proximal and distal ring members.

19. The surgical instrument according to claim 18, wherein the proximal ring member defines an outer annular groove therein, and the proximal end portion of the first articulation shaft has a protrusion slidably received in the annular groove.

20. The surgical instrument according to claim 11, wherein the first and second articulation shafts are rotatable relative to and around the cam member.

* * * * *